(12) United States Patent
Lee et al.

(10) Patent No.: US 10,484,491 B2
(45) Date of Patent: *Nov. 19, 2019

(54) PERSONALIZED MONITORING OF DATA COLLECTED BY THE INTERNET OF THINGS

(71) Applicant: AT&T Intellectual Property I, L.P., Atlanta, GA (US)

(72) Inventors: Tum J. Lee, Oakhurst, NJ (US); Monowar Hossain, Middletown, NJ (US); Thiru Ilango, Holmdel, NJ (US); Gregory C. Sheehan, Toms River, NJ (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/009,293

(22) Filed: Jun. 15, 2018

(65) Prior Publication Data

US 2018/0302481 A1  Oct. 18, 2018

Related U.S. Application Data

(63) Continuation of application No. 15/399,829, filed on Jan. 6, 2017, now Pat. No. 10,009,434, which is a continuation of application No. 15/005,044, filed on Jan. 25, 2016, now Pat. No. 9,560,151, which is a continuation of application No. 13/691,797, filed on Dec. 2, 2012, now Pat. No. 9,268,860.

(51) Int. Cl.
*G06F 15/173* (2006.01)
*H04L 29/08* (2006.01)
*H04L 12/26* (2006.01)
*G06F 16/9535* (2019.01)
*G16H 10/60* (2018.01)
*G06F 19/00* (2018.01)

(52) U.S. Cl.
CPC .......... *H04L 67/22* (2013.01); *G06F 16/9535* (2019.01); *G06F 19/00* (2013.01); *G16H 10/60* (2018.01); *H04L 43/08* (2013.01); *H04L 43/16* (2013.01)

(58) Field of Classification Search
CPC ......... H04L 67/22; H04L 43/16; H04L 43/08; G06F 11/30; G06F 11/34
USPC ....................................................... 709/224
See application file for complete search history.

(56) References Cited

U.S. PATENT DOCUMENTS

| 8,255,529 B2 | 8/2012 | Ferris et al. |
| 8,725,852 B1 * | 5/2014 | Boddu ............... H04L 61/2076 370/221 |
| 2003/0135382 A1 * | 7/2003 | Marejka et al. .................. 705/1 |

(Continued)

FOREIGN PATENT DOCUMENTS

| WO | WO 2008100019 | 8/2008 | | |
| WO | WO-2008100019 A1 * | 8/2008 | ............. | H04L 12/66 |
| WO | WO 2008100019 A1 * | 8/2008 | ............. | H04L 12/66 |

*Primary Examiner* — Hee Soo Kim
(74) *Attorney, Agent, or Firm* — Scott P. Zimmerman, PLLC

(57) ABSTRACT

A personalized data monitoring service is provided to users. Data from a user's devices is collected and compared to user-defined rules and to ranges. Notification messages may be sent to notify of the data. Data labels may be added to explain the data and any abnormal condition.

20 Claims, 19 Drawing Sheets

(56) References Cited

U.S. PATENT DOCUMENTS

| | | | |
|---|---|---|---|
| 2003/0167153 A1* | 9/2003 | Alexander | G06F 19/3418 |
| | | | 702/189 |
| 2007/0121651 A1* | 5/2007 | Casey | H04N 21/440218 |
| | | | 370/401 |
| 2010/0325422 A1 | 12/2010 | Gnanasambandam et al. | |
| 2010/0333116 A1 | 12/2010 | Prahlad et al. | |
| 2011/0107103 A1 | 5/2011 | Dehaan et al. | |
| 2011/0314482 A1* | 12/2011 | Cupala | G06Q 30/00 |
| | | | 719/328 |
| 2012/0011031 A1 | 1/2012 | Lewis et al. | |
| 2012/0047339 A1 | 2/2012 | Decasper et al. | |
| 2012/0066322 A1 | 3/2012 | Yang et al. | |
| 2012/0089523 A1 | 4/2012 | Hurri et al. | |
| 2012/0137003 A1 | 5/2012 | Ferris et al. | |
| 2012/0154141 A1* | 6/2012 | Piccolo, III | G08B 25/14 |
| | | | 340/539.11 |
| 2012/0203733 A1 | 8/2012 | Zhang | |
| 2012/0272266 A1 | 10/2012 | Ou et al. | |
| 2013/0054575 A1* | 2/2013 | Bodin | G06F 16/9577 |
| | | | 707/722 |
| 2013/0120132 A1 | 5/2013 | Hicks, III | |

\* cited by examiner

PERSONALIZED MONITORING OF DATA COLLECTED BY THE INTERNET OF THINGS

CROSS-REFERENCE TO RELATED APPLICATIONS

This application is a continuation of U.S. application Ser. No. 15/399,829 filed Jan. 6, 2017 and since issued as U.S. Pat. No. 10,009,434, which is a continuation of U.S. application Ser. No. 15/005,044 filed Jan. 25, 2016 and since issued as U.S. Pat. No. 9,560,151, which is a continuation of U.S. application Ser. No. 13/691,797 filed Dec. 2, 2012 and since issued as U.S. Pat. No. 9,268,860, with all applications incorporated herein by reference in their entireties.

BACKGROUND

Massive amounts of data are being generated and collected. Each visit to a doctor generates health-related data. Smart phones generate data based on usage and location. Even more data is being generated by stand alone digital devices, communications network devices, home automation devices, security systems, and banking transactions. No individual user can hope to monitor all the data being generated.

BRIEF DESCRIPTION OF THE SEVERAL VIEWS OF THE DRAWINGS

The features, aspects, and advantages of the exemplary embodiments are better understood when the following Detailed Description is read with reference to the accompanying drawings, wherein.

DETAILED DESCRIPTION

The exemplary embodiments will now be described more fully hereinafter with reference to the accompanying drawings. The exemplary embodiments may, however, be embodied in many different forms and should not be construed as limited to the embodiments set forth herein. These embodiments are provided so that this disclosure will be thorough and complete and will fully convey the exemplary embodiments to those of ordinary skill in the art. Moreover, all statements herein reciting embodiments, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and the like represent conceptual views or processes illustrating the exemplary embodiments. The functions of the various elements shown in the figures may be provided through the use of dedicated hardware as well as hardware capable of executing associated software. Those of ordinary skill in the art further understand that the exemplary hardware, software, processes, methods, and/or operating systems described herein are for illustrative purposes and, thus, are not intended to be limited to any particular named manufacturer.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will also be understood that, although the terms first, second, etc. may be used herein to describe various elements, these elements should not be limited by these terms. These terms are only used to distinguish one element from another. For example, a first device could be termed a second device, and, similarly, a second device could be termed a first device without departing from the teachings of the disclosure.

Figure 1:
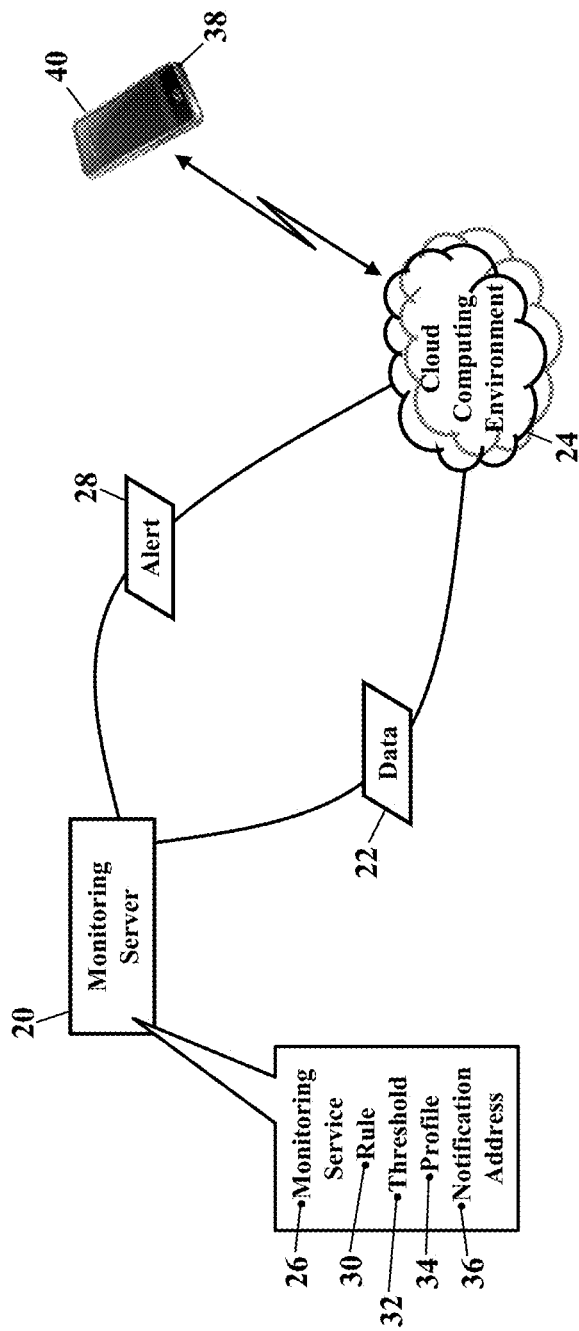
FIG. 1 is a simplified schematic illustrating an environment in which exemplary embodiments may be implemented.

FIG. 1 is a simplified schematic illustrating an environment in which exemplary embodiments may be implemented. FIG. 1 illustrates a monitoring server 20 collecting data 22 in a cloud computing environment 24. The monitoring server 20 provides a monitoring service 26 that sends an alert 28 when the data 22 satisfies some rule 30 and/or threshold 32. The data 22 may be any information that a user wishes monitored, such as computer system information, computer application information, electronic health information, location information, and environmental information. The data 22, as a simple example, may be generated by a data server that sends the data 22 asynchronously, in a one direction outgoing broadcast flow, to the monitoring server 20. The data server, in other words, may not respond to a network query. An example of an asynchronous data server is a temperature monitoring device that broadcasts the temperature measurement periodically, such as once every 10 seconds. The user may establish a profile 34 that specifies what data 22 is collected and how the data 22 is compared to the rule 30 and/or threshold 32. Whatever the data 22, the monitoring service 26 determines when the data 22 is abnormal, according to the user's self-defined rule 30 and/or threshold 32. When the data 22 satisfies the user's rule 30 and/or threshold 32, the monitoring service 26 may send the alert 28. The alert 28 may contain information on the data 22 that triggered the rule 30, and information associated with the data 22. The alert 28 is sent to a notification address 36, again as determined by the user's profile 34. That is, the monitoring service 26 allows the user to define who (or what notification addresses 36) is informed when the data 22 is determined abnormal, exceptional, or outside desired ranges. FIG. 1, for simplicity, illustrates the alert 28 routing to the notification address 36 associated with any notification device 38, such as a user's smart phone 40.

Exemplary embodiments thus provide the cloud-based monitoring service 26. The user's personal data 22 is stored and compared to the user's self-defined rules 30 for triggering the alert 28. The alert 28 may be sent to any recipient(s) the user desires. Exemplary embodiments may even share the data 22 with any recipient, such as local and remote care givers and other service providers. The monitoring service 26 thus allows the user to keep trusted ones informed of any personal data, such as medical, security, and financial information. The monitoring service 26, however, may also track and inform of any data, such as business information, computer system information, and computer network information. The monitoring service 26 may even provide predefined tools for analyzing the data 22, such as statistical analysis that summarizes the data 22.

The data 22 may be generated by any device. The data 22, for example, may be collected by a networked device that captures the data 22 from a stand-alone networked or non-networked device. The data 22 may also be collected by, or transmitted from, a device with localized communication links, and even a complex home automation system with communication links to the Internet. The monitoring server 20 may even collect the data 22 from third-party service providers, such communications, banking, health care, and security services. Some examples of the data 22 generated by devices include computer, computer application, landline or wireless telecommunications network equipment, commercial or DC power level and frequency monitor, audio noise monitor, radio frequency wideband or narrow-band noise monitor, optoelectronic signal monitor, temperature station, smoke/CO2 detectors, personal weather station, personal emergency alert device, perimeter video surveillance camera, blood pressure machine, water leak detector, wireless pill bottle, wireless armband collecting health and fitness data, home automation system, medical monitoring devices such as wireless diabetics meters, smart phone data usage and battery monitoring applications, and GPS location application.

The monitoring service 26 thus helps manage the user's business and personal data 22. As more and more devices collect the data 22, the volume of the data 22 grows, especially in today's mobile environment. Monitoring and analysis of that data 22 can be an overwhelming task. Exemplary embodiments, though, automate the monitoring and analysis functions, thus providing the user with a simple and configurable service. Much of the data 22 may be routine and within normal expectations. However, one person's "normal" range could be "abnormal" to another person. Exemplary embodiments thus permit the user to self-define the data 22 they wish to be monitored, along with the rules 30 and/or thresholds 32 that determine when the alert 28 is sent. That is, the user may configure their own ranges of abnormal or exceptional data 22. Exemplary embodiments provide a turn-key monitoring service 26 that collects, correlates, and even translates the user's personal data 22 into actionable information specific to the user's interests.

The monitoring service 26 is rule-based. The monitoring service 26 is deployed to provide the user with rule-based features that identify the data 22 that needs attention by one or more recipients. The monitoring service 26 may provide access to an integrated view of the user's own data 22. The user may update the notification addresses 36 in the user's profile 34 using this integrated solution. The user may define the rules 30 and thresholds 32, thus allowing the user to self-determine what data conditions require the alert 28. The user may even manage a recipient list of the notification addresses 36, thus defining different message formats for different recipients. Some recipients may receive a simple text message, while other recipients may receive pictures and even video data. Distribution lists may even be defined, thus alerting some recipients via email, TWITTER®, text message, instant messaging, voice message, or other account. The rules 30 may even be defined to suppress spurious false alarms.

The user's profile 34 is self-configured. The user determines what data 22 is collected, and how the collected data 22 is monitored. The user may thus construct and personalize the rules 30 that translate exceptional data 22 into the personalized, actionable alert 28. Both the rules 30 and the threshold 32 may have dependence on time of day, and calendar dependence by day of week and month of year, and/or season of the year. The cloud-based monitoring server 20 collects, stores, and processes the user's desired data 22. The monitoring server 20 may also have a web-based interface that permits the user to manage the profile 34 and to view a history of the alerts 28 previously sent to recipients.

Figure 2:
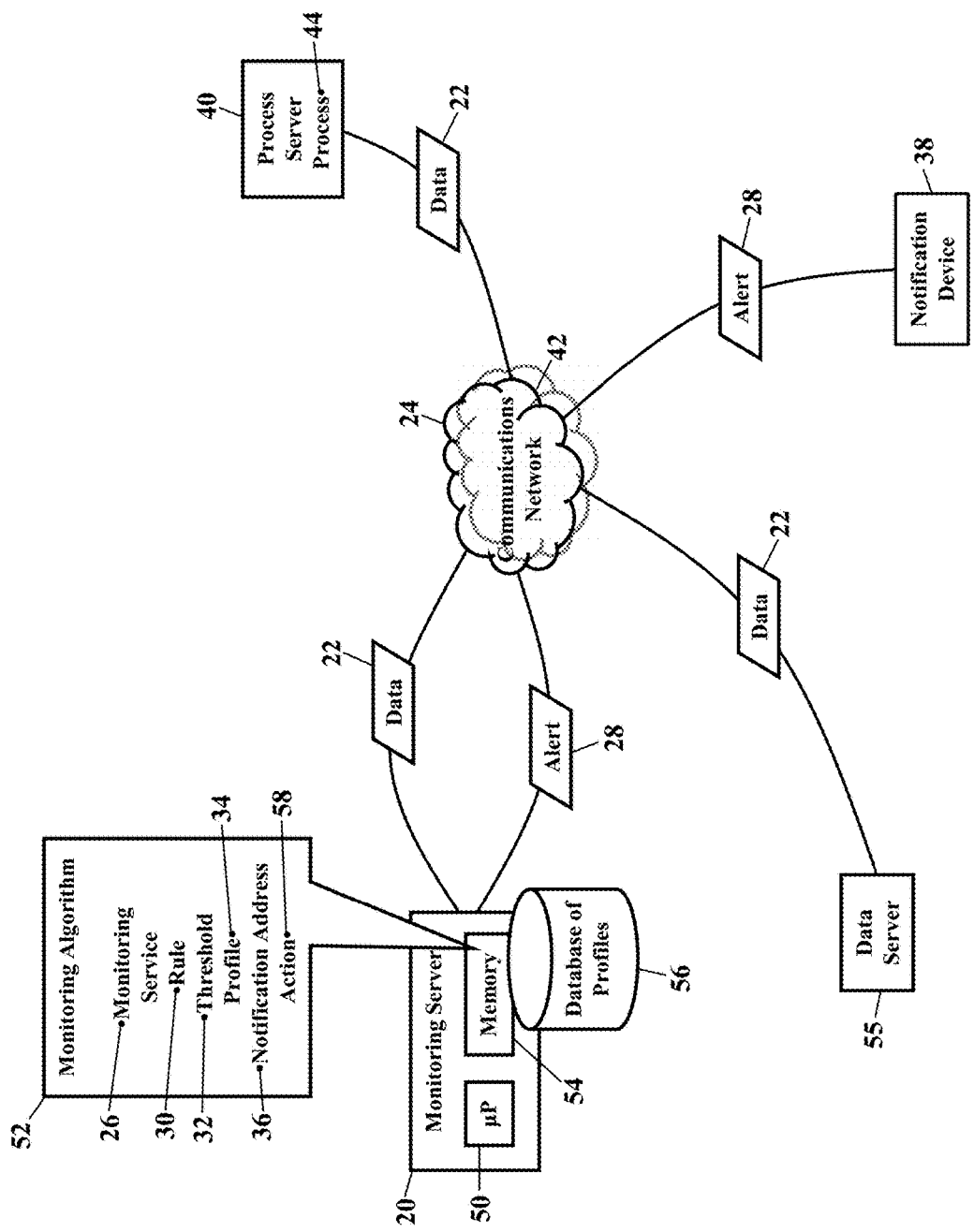
FIG. 2 is a more detailed block diagram illustrating the operating environment, according to exemplary embodiments.

FIG. 2 is a more detailed block diagram illustrating the operating environment, according to exemplary embodiments. Here the monitoring server 20 communicates with a process server 40 via the cloud computing environment 24. The cloud computing environment 24 is illustrated as a communications network 42. The process server 40 executes any process 44 that generates the data 22. The monitoring server 20 queries the process server 40 to obtain the data 22. The monitoring server 20 has a processor 50 (e.g., "μP"), application specific integrated circuit (ASIC), or other component that executes a monitoring algorithm 52 stored in a memory 54. The monitoring algorithm 52 instructs the processor 50 to query the process server 40 for the data 22 specified by the user's profile 34. The user's profile 34 may be retrieved from a database 56 of profiles. FIG. 2 illustrates the database 56 of profiles as being locally stored in the memory 54 of the monitoring server 20. The database 56 of profiles, however, may be remotely stored and accessed from any network location in the communications network 42. Once the data 22 is retrieved, the monitoring algorithm 52 instructs the processor 50 to compare the data 22 to the rules 30 and thresholds 32 defined in the user's profile 34. If the data 22 satisfies the rules 30 and/or thresholds 32, the monitoring algorithm 52 instructs the processor 50 to execute an associated action 58. The action 58, for example, may include sending the alert 28 to the notification address 36 specified by the user's profile 34.

The data 22 may also be received from a data server 55. The data server 55 receives and accumulates the data 22 from any source. The data server 55 may then send or transfer the data 22 to the monitoring server 20. The data 22 may be periodically sent according to date and time, or the data 22 may be randomly sent when conditions warrant. When the monitoring server 20 receives the data 22 from the data server 55, the monitoring algorithm 52 may again instruct the processor 50 to compare the data 22 to the rules 30 and thresholds 32 defined in the user's profile 34. If the data 22 from the data server 55 satisfies the rules 30 and/or thresholds 32, the associated action 58 may be executed, such as sending the alert 28. Here, though, exemplary embodiments may analyze different combinations of the data 22 received from the process server 40 and the data server 55. Different time periods, for example, may be established, such that the process server 40 and the data server 55 may be queried at different times of day or according to different periods of time. The rule 30 may require different percentages of the data 22 be retrieved and combined from the process server 40 and from the data server 55. That is, the monitoring algorithm 52 may retrieve and combine different combinations of the data 22 from the process server 40 and from the data server 55, according to the user's rule 30. The rule 30 may also require a historical evaluation of the data 22 from the process server 40 and from the data server 55, perhaps according to different intervals of time. As an example, the rule 30 may require combining three (3) instances of high values of the data 22 from the process server 40 occurring within the past hour with two (2) instances of high values from the data server 55 occurring within the past hour. Another example of the rule 30, a single occurrence of the data 22 within the past fifteen (15) minutes from the data server 55 may be combined with three (3) occurrences of the data 22 from the process server 40 occurring within the last two (2) hours.

Exemplary embodiments, though, may be applied regardless of networking environment. As the above paragraphs mentioned, the communications network 42 may be a wireless network having cellular or WI-FI® capabilities. The communications network 42, however, may also operate using any other frequency or standard, such as the BLUETOOTH® standard or the Internet Protocol (IP). The communications network 42, however, may be a cable network operating in the radio-frequency domain and/or the Internet Protocol (IP) domain. The communications network 42, however, may also include a distributed computing network, such as the Internet (sometimes alternatively known as the "World Wide Web"), an intranet, a local-area network (LAN), and/or a wide-area network (WAN). The communications network 42 may include terrestrial or satellite radio frequency transmission, coaxial cables, copper wires, fiber optic lines, and/or hybrid-coaxial lines. The communications network 42 may even include wireless portions utilizing any portion of the electromagnetic spectrum and any signaling standard (such as the IEEE 802 family of standards, GSM/CDMA/TDMA or any cellular standard, and/or the ISM band). The communications network 42 may even include powerline portions, in which signals are communicated via electrical wiring. The concepts described herein may be applied to any wireless/wireline communications network, regardless of physical componentry, physical configuration, or communications standard(s).

Figure 3:
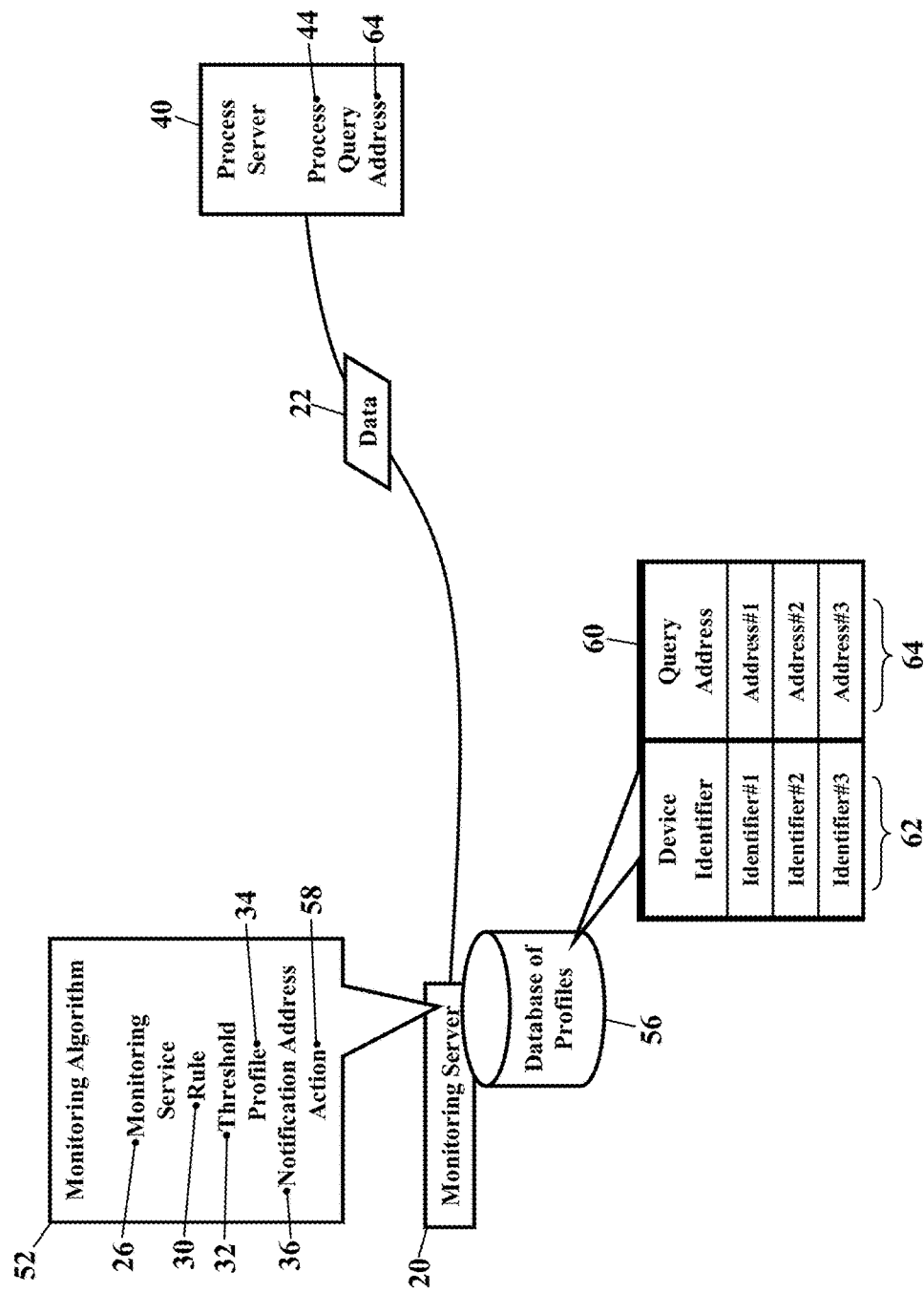
FIG. 3 is a detailed diagram illustrating a profile, according to exemplary embodiments.

FIG. 3 is a more detailed diagram illustrating the profile 34, according to exemplary embodiments. If the user wishes to subscribe to the monitoring service 26, the user may be prompted to define the profile 34. The user, for example, completes some registration or set-up phase that determines what data 22 the user wishes collected and monitored. The user selects what data 22, from what devices, is monitored. The profile 34, for example, may store a table 60 that lists device identifiers 62. Each monitored device is uniquely identified by its associated device identifier 62. The user selects the device identifier 62 that corresponds to the device to be monitored.

FIG. 3 also illustrates query addresses 64. Once the user selects or enters the device identifier 62, the monitoring server 20 needs to know from where the data 22 is retrieved. The profile 34 may thus also specify the query address 64 associated with each device identifier 62. The table 60 maps, relates, or otherwise associates the device identifier 62 to its corresponding query address 64. The query address 64 is any network address (such as an Internet Protocol address) from which the data 22 is retrieved, such as the process server 40. The process server 40 executes some process 44 that stores the data 22 generated by the corresponding device identifier 62. The profile 34 may thus be populated with the device identifiers 62 to be monitored and their corresponding query addresses 64.

Figure 4:
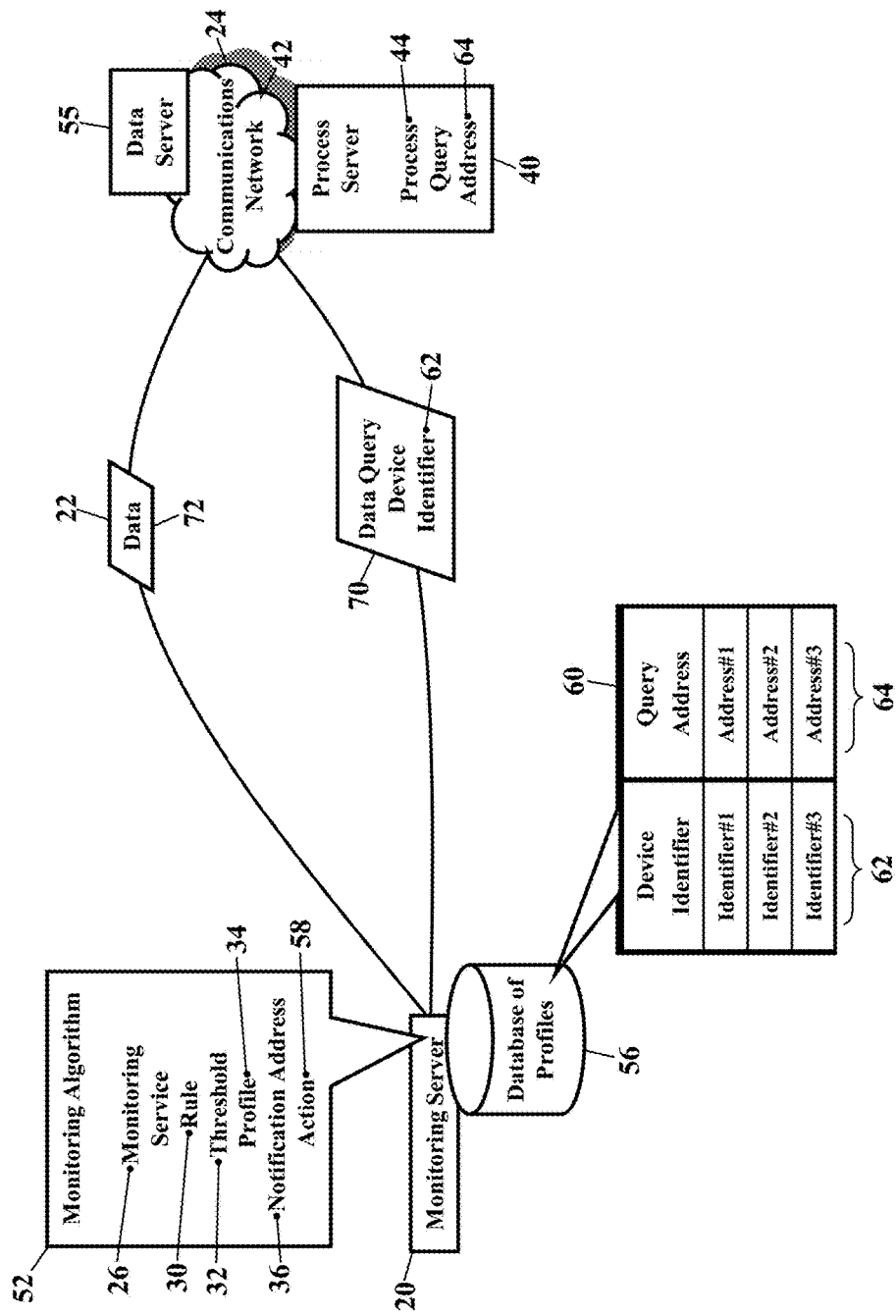
FIG. 4 is a schematic illustrating data queries, according to exemplary embodiments.

FIG. 4 is a schematic illustrating data queries, according to exemplary embodiments. Once the monitoring service 26 is established, the monitoring server 20 sends a data query 70 to the query address 64 identified in the profile 34. The data query 70 routes along the communications network (illustrated as reference numeral 42 in FIG. 2) to the query address 64 associated with the process server 40 and/or the data server 55 that stores the desired data 22. When the data query 70 is received, the data 22 is retrieved that is associated with the device identifier 62. The data 22 is sent in a response 72. The response 72 routes along the communications network 42 to the network address associated with the monitoring server 20. The monitoring server 20 stores the data 22 for analysis. As earlier paragraphs explained, though, either the process server 40 and/or the data server 55 may asynchronously the data 22 without being queried.

Figure 5:
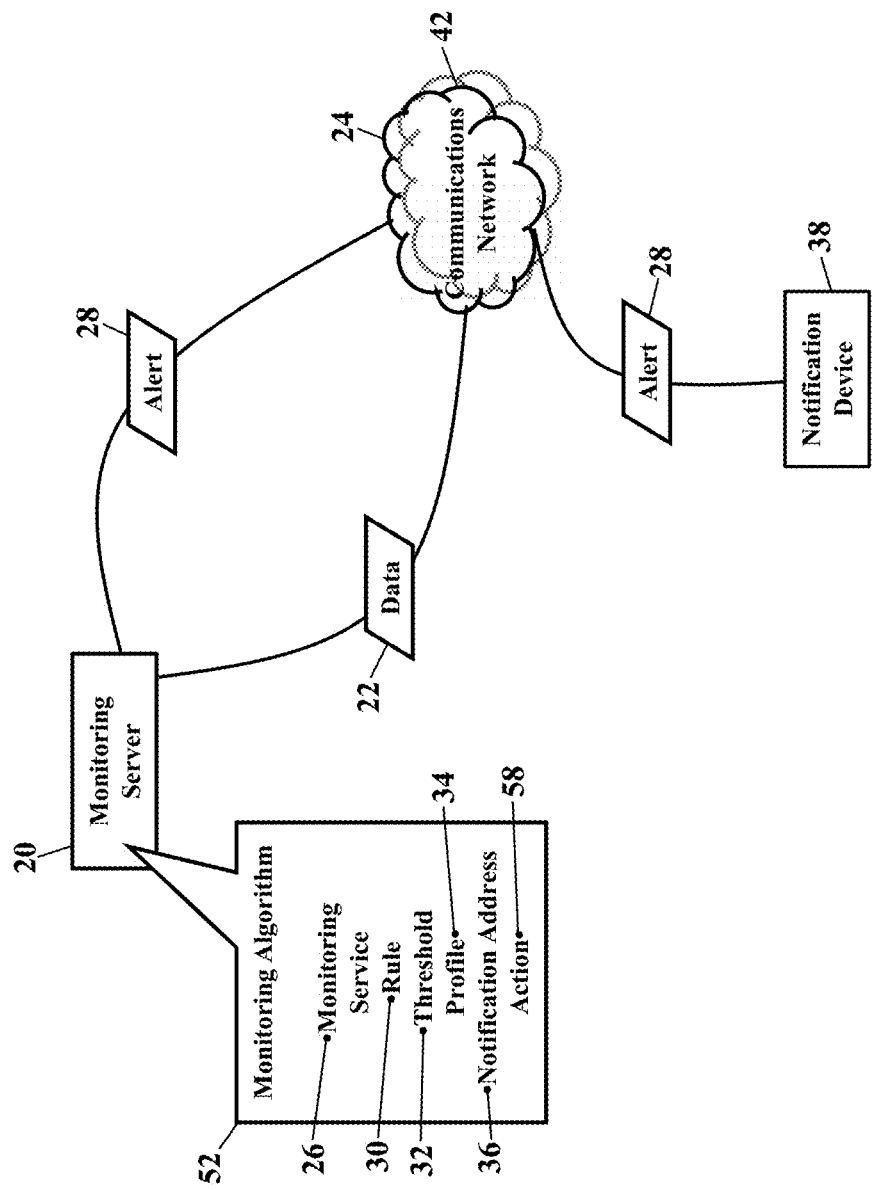
FIG. 5 is a schematic illustrating a monitoring service, according to exemplary embodiments.

FIG. 5 is another schematic illustrating the monitoring service 26, according to exemplary embodiments. Now that the data 22 is retrieved, the monitoring server 20 determines if the data 22 is within limits defined by the user. The monitoring server 20 queries the profile 34 for the user's self-defined rule 30 and/or threshold 32. Because the data 22 is personal, the user defines and constructs the rules 30 and thresholds 32. Some users may be avid runners, so they do not care if their heart rate exceeds 100 beats per minute. Other users, though, may be alarmed when their heart rate exceeds 100 beats per minute. The user may thus personalize the rule 30 and threshold 32 according to their desires, history, and activities. The user may also personalize the notification address(es) 36 associated with each rule 30. The user may thus define who gets the alert 28 when the data 22 lies out-of-bounds. The monitoring server 20 compares the data 22 to the user's self-defined rule 30 and/or threshold 32. When the data 22 satisfies the threshold 32, the rule 30 may require the alert 28 to the personalized notification address 36 associated with the notification device 38.

Figure 6:
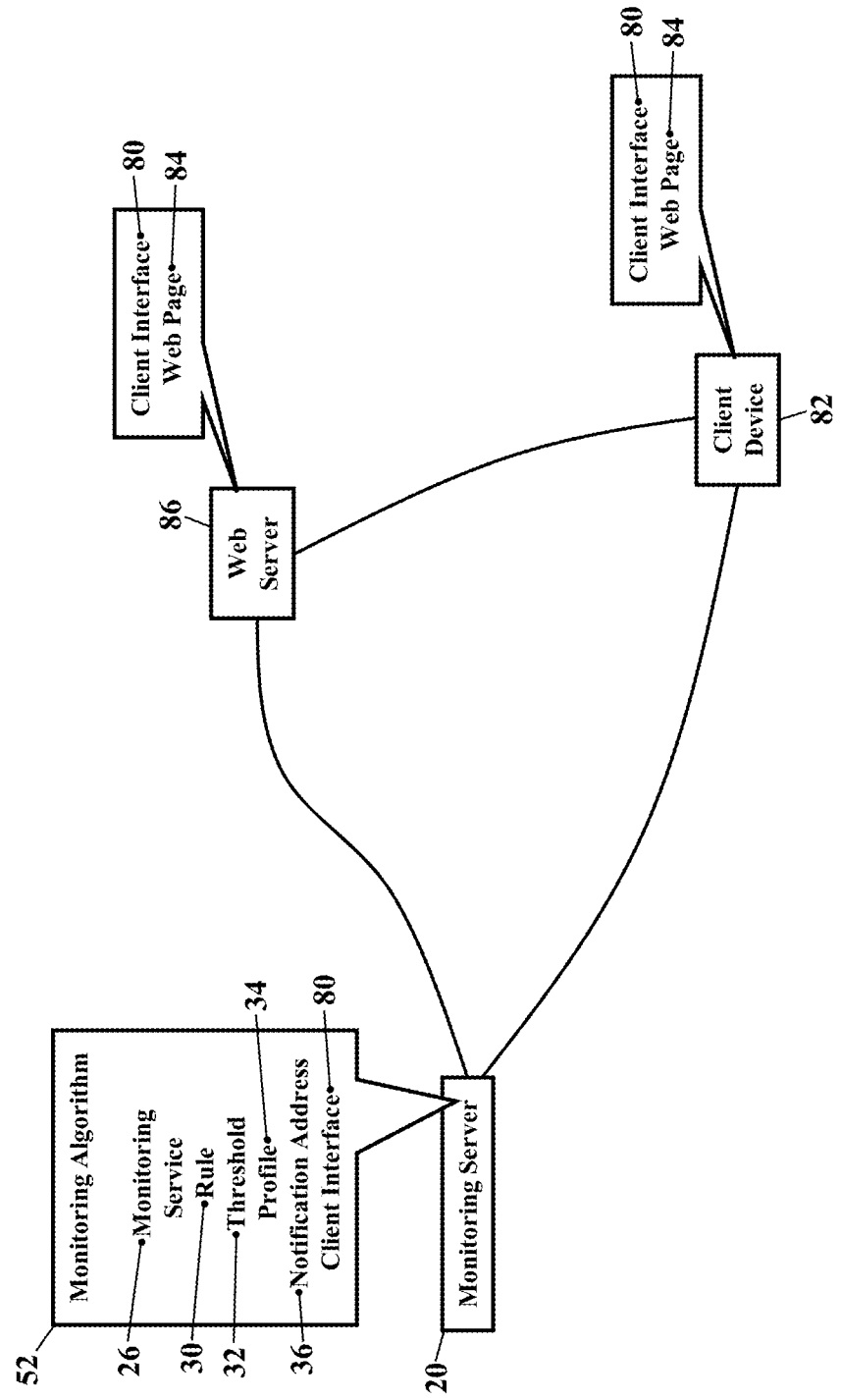
FIG. 6 is a schematic illustrating a client interface for the monitoring service, according to exemplary embodiments.

FIG. 6 is a schematic illustrating a client interface 80 for the monitoring service 26, according to exemplary embodiments. The client interface 80 allows the user, from any client device 82, to configure the monitoring service 26. FIG. 6 illustrates the client interface 80 as a web page 84 generated or assembled by a web server 86. When, for example, the user wishes to access her profile 34, the client device 82 sends a request to the web server 86. The monitoring server 20 and the web server 86 cooperate to generate the client interface 80. The web server 86 may transform the client interface 80 into the web page 84. The web server 86 sends the web page 84 to the client device 82, and the web page 84 includes information describing the client interface 80. The monitoring server 20, however, may optionally send the client interface 80 directly to the network address associated with the client device 82. Regardless, the client interface 80 allows the user, at the client device 82, to configure the monitoring service 26. The client interface 80, for example, may be a digital dashboard that displays the user's personalized profile 34. The user may thus make inputs that change the device identifier 62, the query address 64, the rule 30, the threshold 32, and/or the notification address 36. Whatever changes are made, the profile 34 is updated in the database 56 of profiles.

Figure 7:
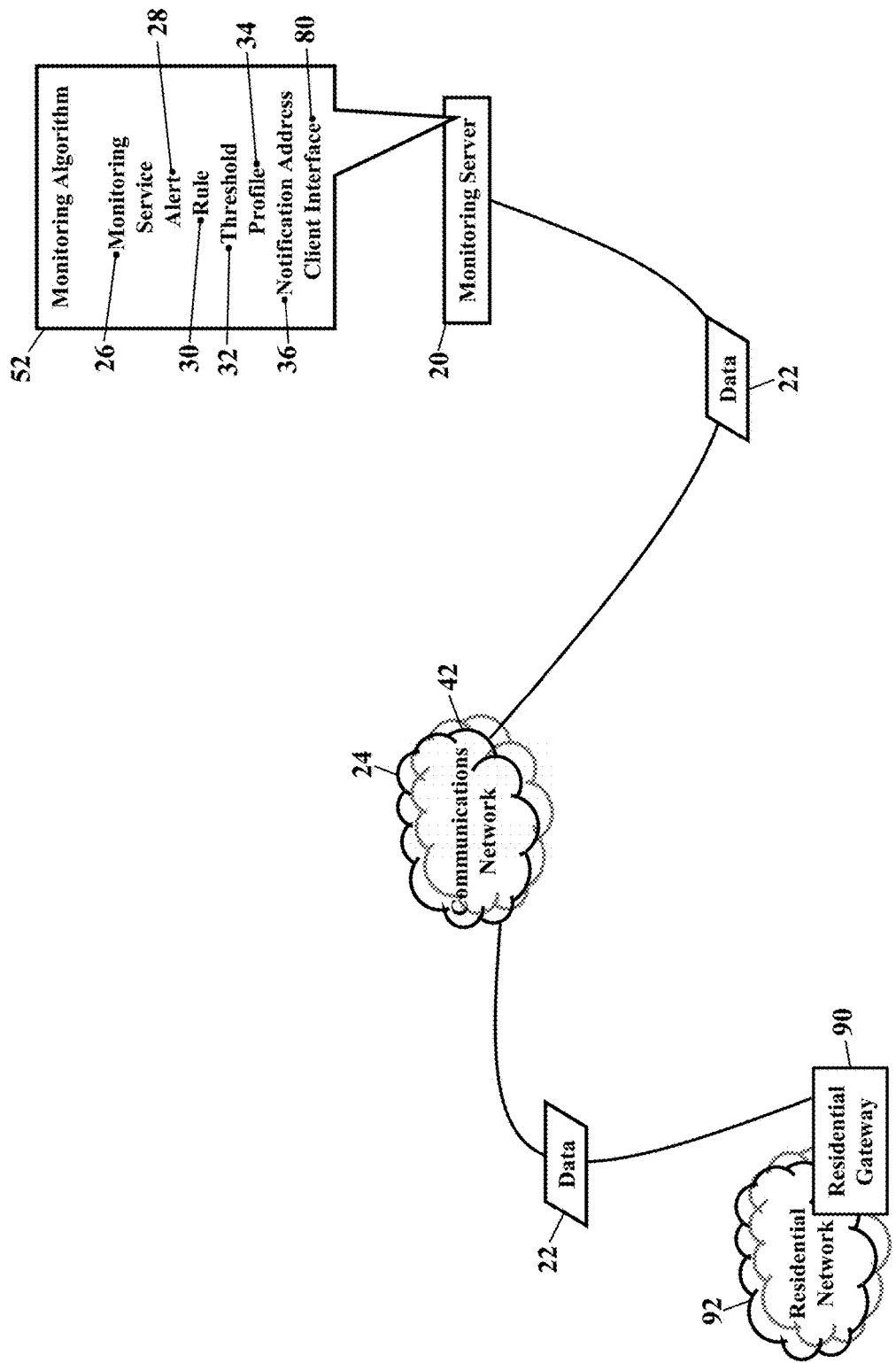
FIG. 7 is a schematic illustrating a service ecosystem, according to exemplary embodiments.

FIG. 7 is a schematic illustrating a service ecosystem, according to exemplary embodiments. Here a wireless residential gateway 90 in a residential network 92 sends environmental data 22 to the monitoring server 20. The user's profile 34 defines what data 22 is collected and stored. The monitoring server 20 then monitors the data 22, according to the user's profile 34. The user configures the profile 34 to determine how the data 22 is processed. Moreover, the user normalizes the data 22 by establishing the rules 30 and thresholds 32 for interpreting normal or abnormal conditions. The monitoring service 26 may provide templates for the user to configure with default values. However, the user may configure their own data limits that determine when the alert 28 is sent. The client interface 80 also allows the user to identify the notification addresses 36 of the recipients. The user thus selects what data 22 is analyzed, how that data 22 is normalized, and what data 22 requires the alert 28 and/or distribution. Exemplary embodiments thus describe a simple solution for complex monitoring. Because the monitoring service 26 is centralized and cloud-based, the user may specify the collection of the data 22 from any networked device, server, of third party service provider.

Figure 8:
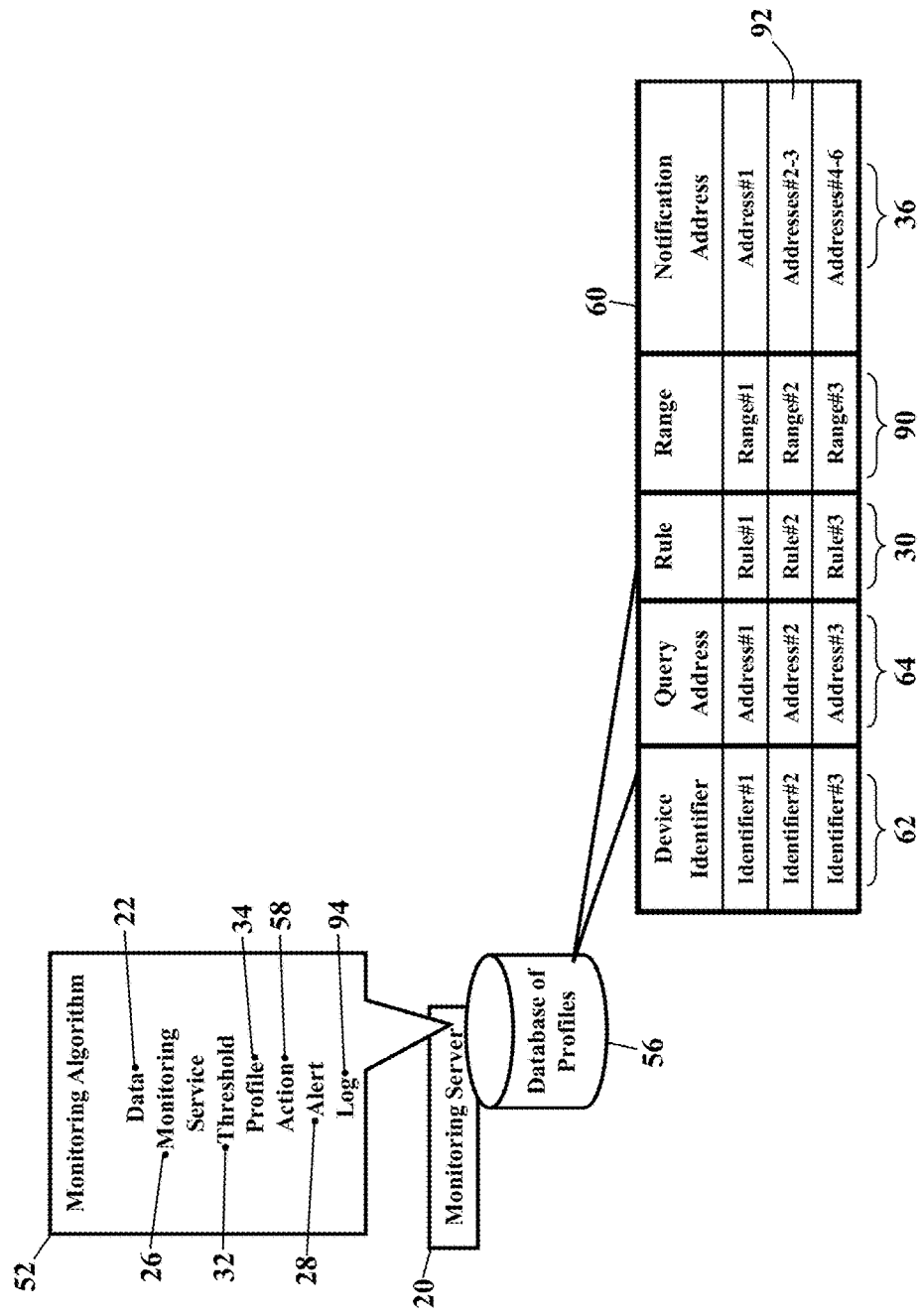
FIGS. 8-9 are schematics illustrating personalized rules, according to exemplary embodiments.
Figure 9:
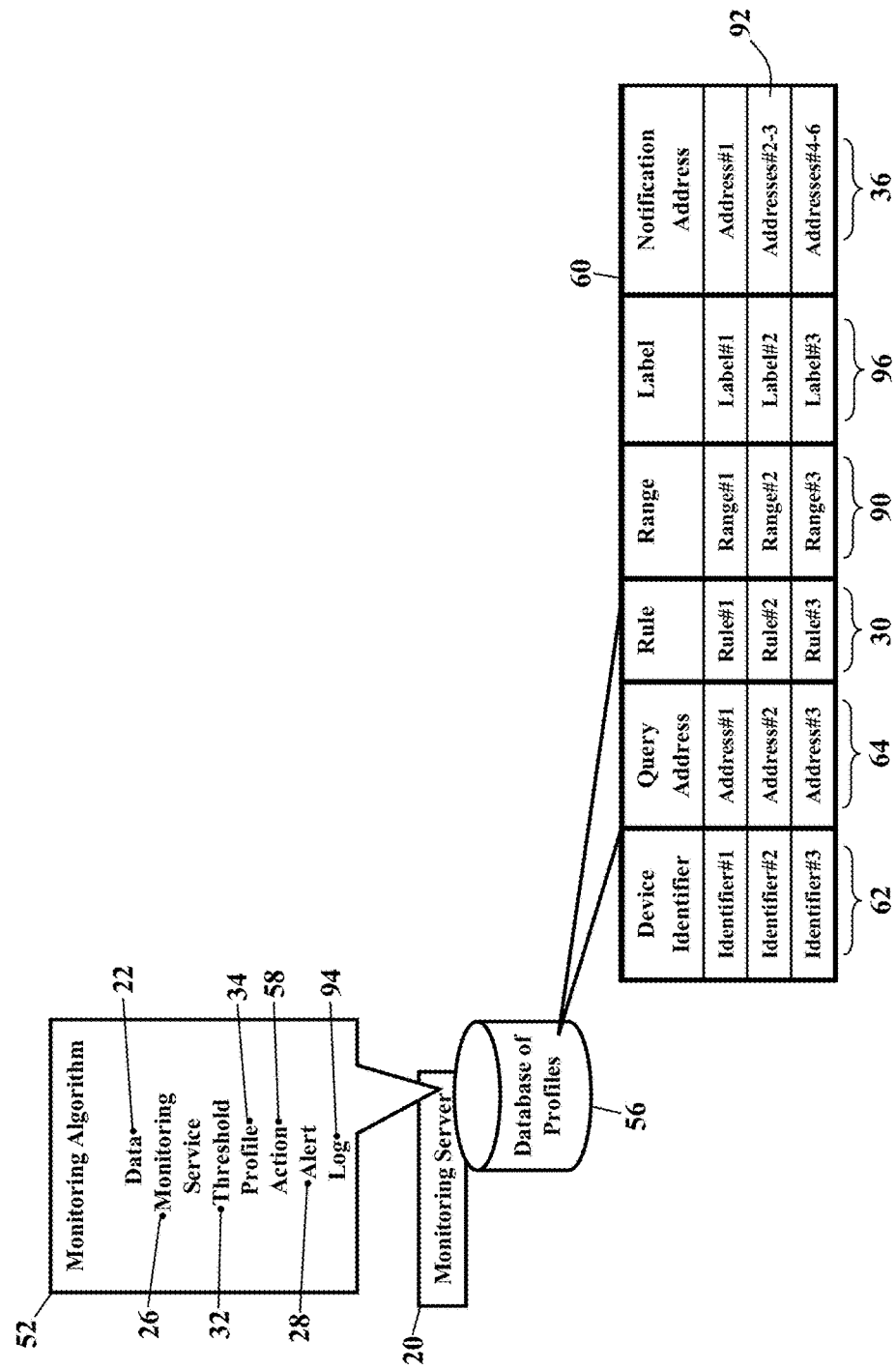

FIGS. 8-9 are schematics further illustrating the personalized rules 30, according to exemplary embodiments. Because the rules 30 and thresholds 32 may be personalized, here the user may define a range 90 of the data 22 for normal and/or abnormal conditions. FIG. 8, for example, again illustrates the profile 34 stored in the database 56 of profiles. The table 60 may include entries that associate the range 90 of the data 22 to the device identifier 62 and to the rule 30. As the monitoring algorithm 52 executes the rule 30, the monitoring algorithm 52 retrieves the corresponding user-defined range 90 of the data 22. The processor 50 compares the data 22 to the range 90 that is personalized by the user's profile 34. When the data 22 satisfies the range 90, the profile 34 may also include an entry defining the action 58 to implement. The action 58, for example, may require retrieving a list 92 of the notification addresses 36. The monitoring algorithm 52 may thus cause the notification 28 to be sent to each recipient in the list 92 of the notification addresses 36. The monitoring algorithm 52 may also store, maintain, and update a log 94 of each alert 28 sent to each notification address 36, perhaps according to date and time.

FIG. 9 illustrates a label 96 for the range 90 of the data 22. Here the user may also define the label 96 that is associated with the corresponding range 90 of the data 22. When the user defines the range 90 of the data 22, the user may also associate her desired label 96 in the profile 34. The label 96 thus helps discern the data 22 and/or the range 90 of the data 22. When the monitoring server 20 determines that the data 22 satisfies the range 90 of the data 22, the monitoring algorithm 52 may cause the monitoring server 20 to retrieve and to send the label 96 to any recipient at the notification address(es) 36.

The label 96 may be explanatory. The label 96, in simple terms, may help explain to the recipient what data is out-of-bounds. The raw data 22 may be complicated or even indecipherable to the recipient. The label 96, though, may present a simple textual or visual description of the data 22, such as "heart rate," "house temp," or "location of Mom's phone." The label 96 may even be more descriptive, such as "heart rate is too high" or "water in basement." The user may thus define the label 96 to summarize the out-of-bounds data 22. The user may thus map a range of values of the data 22 to the label 96 for a simpler visual display that is more meaningful to the user. The display label 96 helps the user to visualize and categories the actual values of the data 22. For example, the user may map values of "0 to 9.99" as "Low," data values "10 to 14.99" as "Medium," and data values "15 to 18.99" as "High." Indeed, the user may even establish the label 96 as "Very High" for values of "19 or greater." In this example, the rule 30 may thus specify two (2) instances of "High" values, and the threshold is 19.

Figure 10:
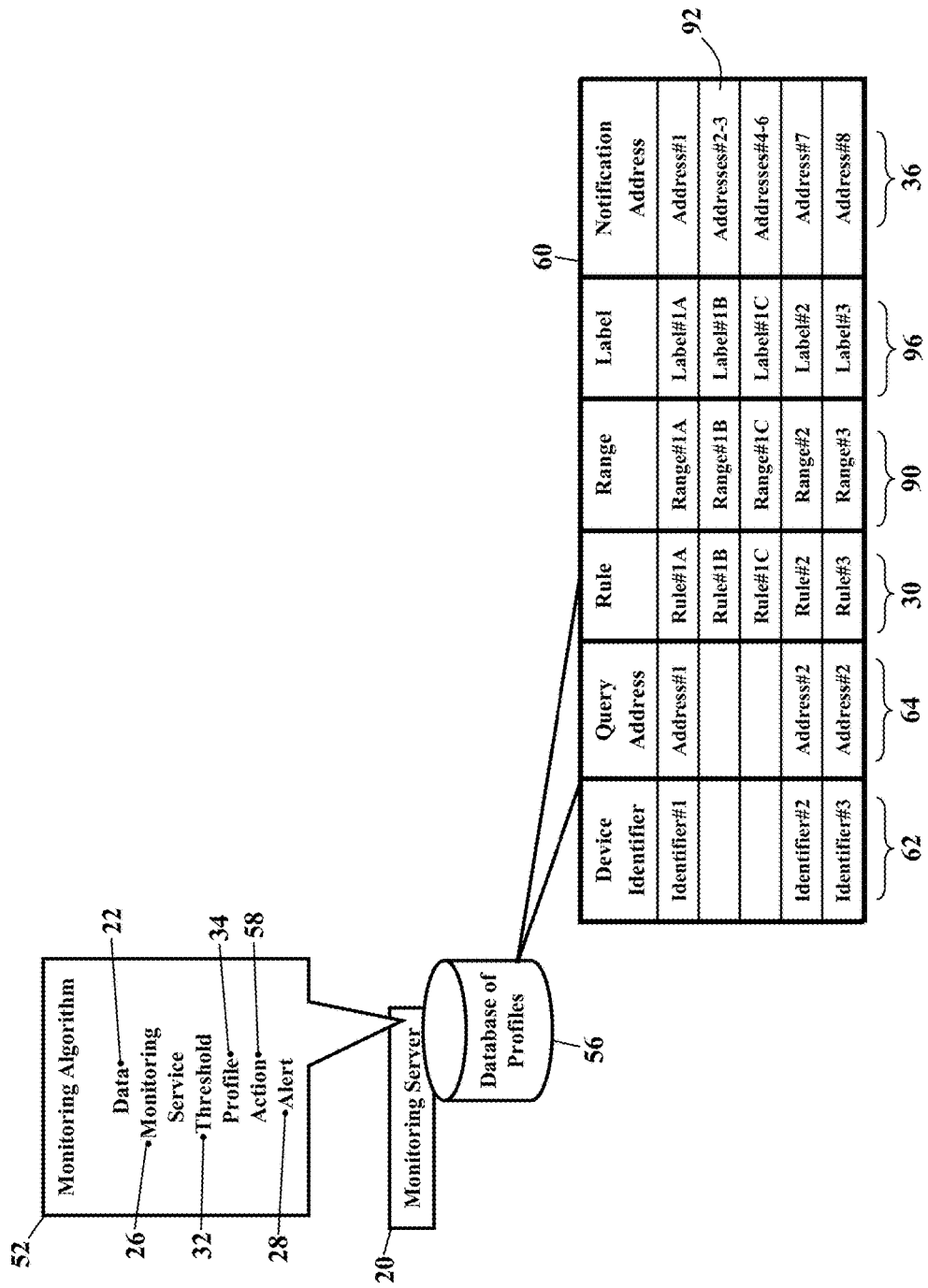
FIG. 10 is a schematic illustrating multiple data ranges, according to exemplary embodiments.

FIG. 10 is a schematic illustrating multiple data ranges, according to exemplary embodiments. Here the user may define multiple ranges 90 of the data 22 from the same device identifier 62. The user may configure the profile 34 with different rules 30 that are applied to the same or different sets of the data 22. Each different rule 30 may have its own corresponding range 90 of the data 22. The monitoring server 20 retrieves and compares the multiple ranges 90 to the data 22 associated with the device identifier 62. When the data 22 satisfies any one of the ranges 90 of the data 22, the monitoring server 20 retrieves the corresponding label 96 and the action 58. The monitoring algorithm 52 instructs the processor 50 to execute the action 58, such as sending the label 96 in the alert 28 to each of the notification addresses 36. Exemplary embodiments may thus permit different actions 58 based on which range 90 of the data 22 is satisfied.

Exemplary embodiments thus permit the user to completely define the actionable rules 30. Each rule 30 may be constructed from the entries in the user's profile 34. The user may separately define the ranges 90 of the data 22 that are actionable. Different recipients may be assigned to each range 90 of the data 22, and the corresponding label 96 helps summarize the alert 28 for ease of explanation.

Figure 11:
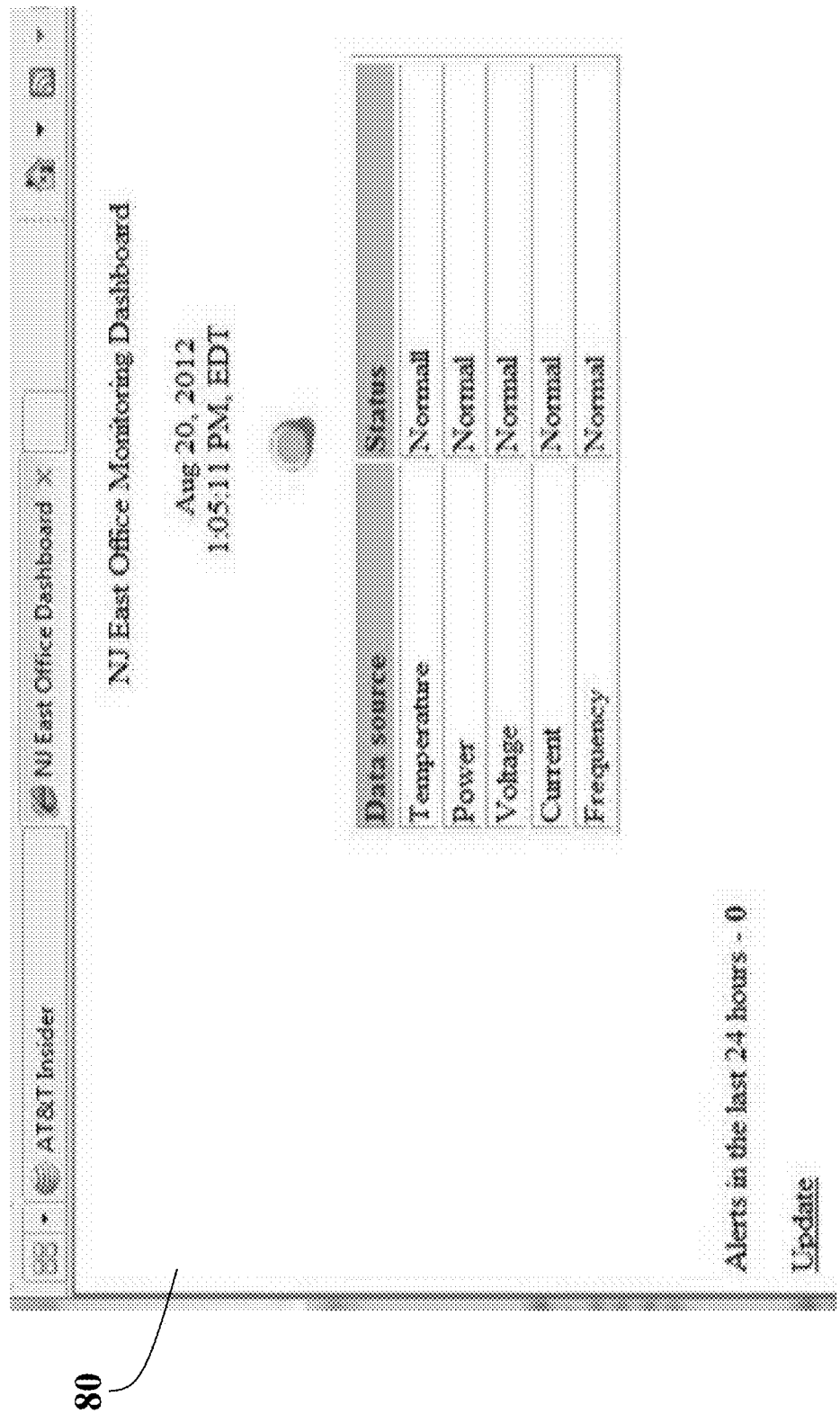
FIGS. 11-13 are graphical illustrations of the client interface, according to exemplary embodiments.
Figure 12:
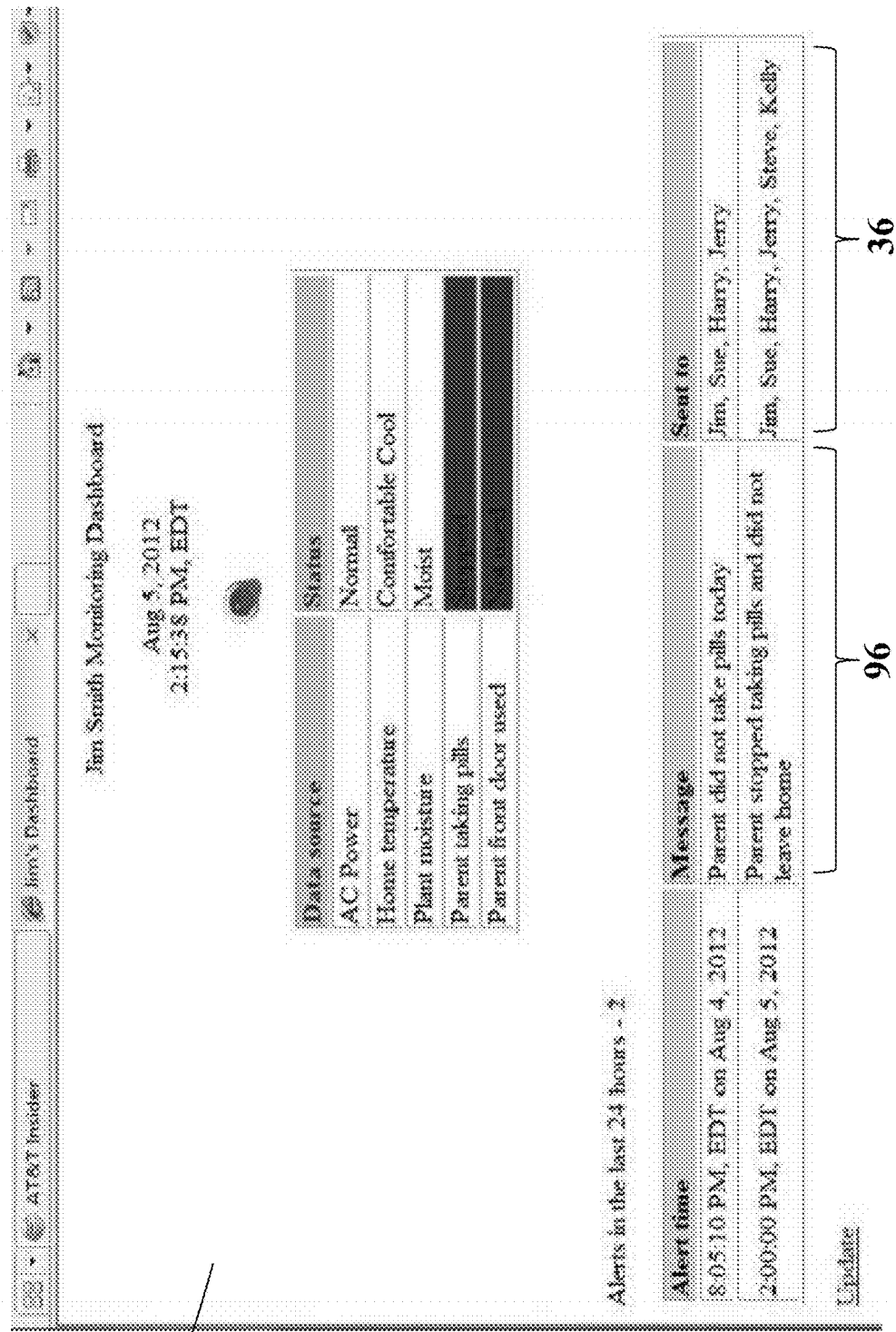
Figure 13:
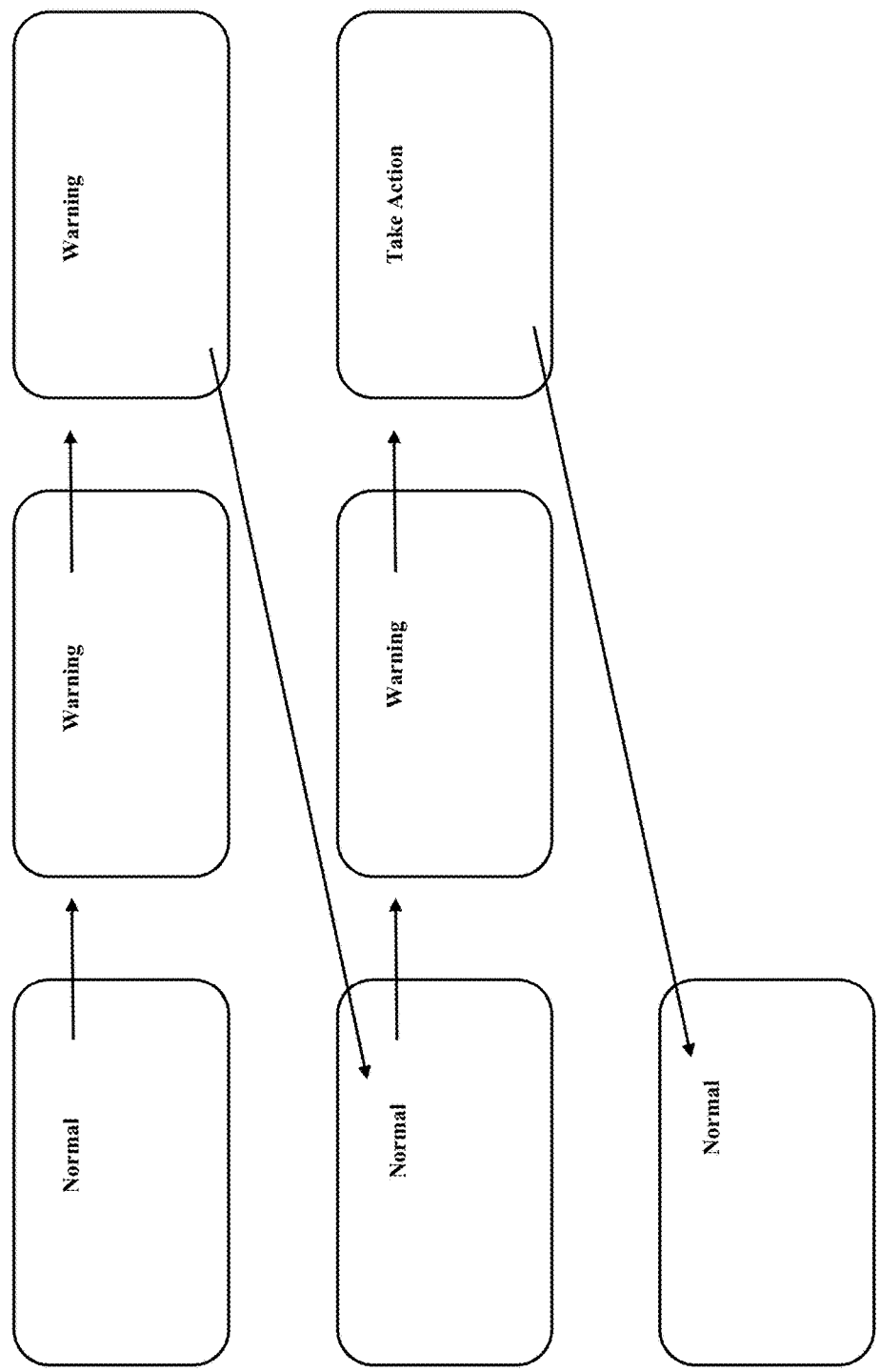

FIGS. 11-13 are graphical illustrations of the client interface 80, according to exemplary embodiments. FIGS. 11-13 illustrates the client interface 80 as a graphical user interface visually displayed on any display device. The client interface 80 allows the user to view status and summary of the monitored data 22. Data within tolerances may be reported as normal, while the data outside the user-defined ranges may be labeled as desired by the user. FIG. 12, for example, illustrates the label 96 that is retrieved and sent in a message to the recipients at the notification addresses 36. The label 96 provides a personalized description of the data 22, the actual data values, and/or the range that triggered the alert 28. FIG. 13 illustrates how the profile 34 may be configured to escalate alerts to help ensure corrective action is taken.

Figure 14:
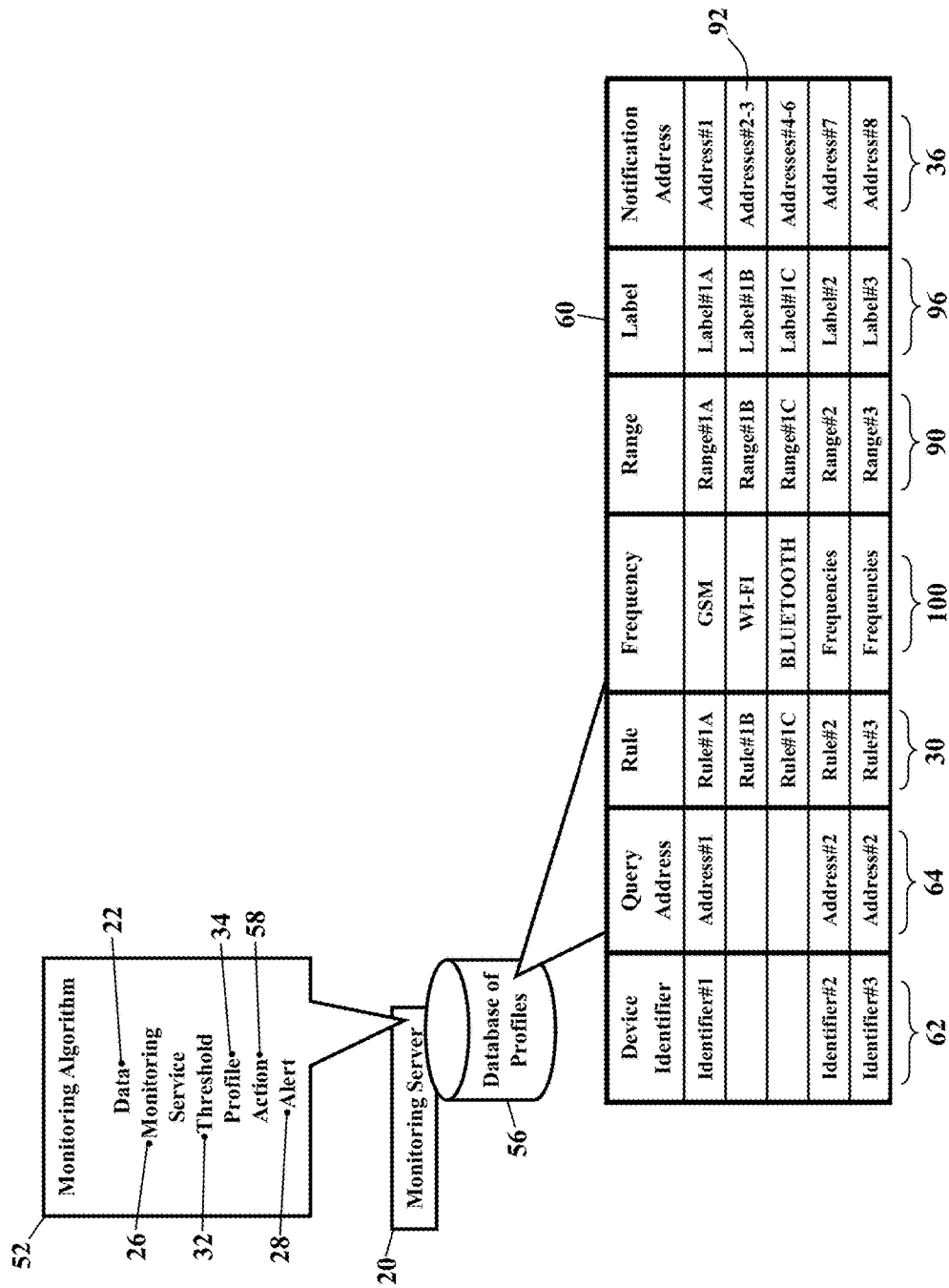
FIGS. 14-15 are more schematics illustrating the profile, according to exemplary embodiments.
Figure 15:
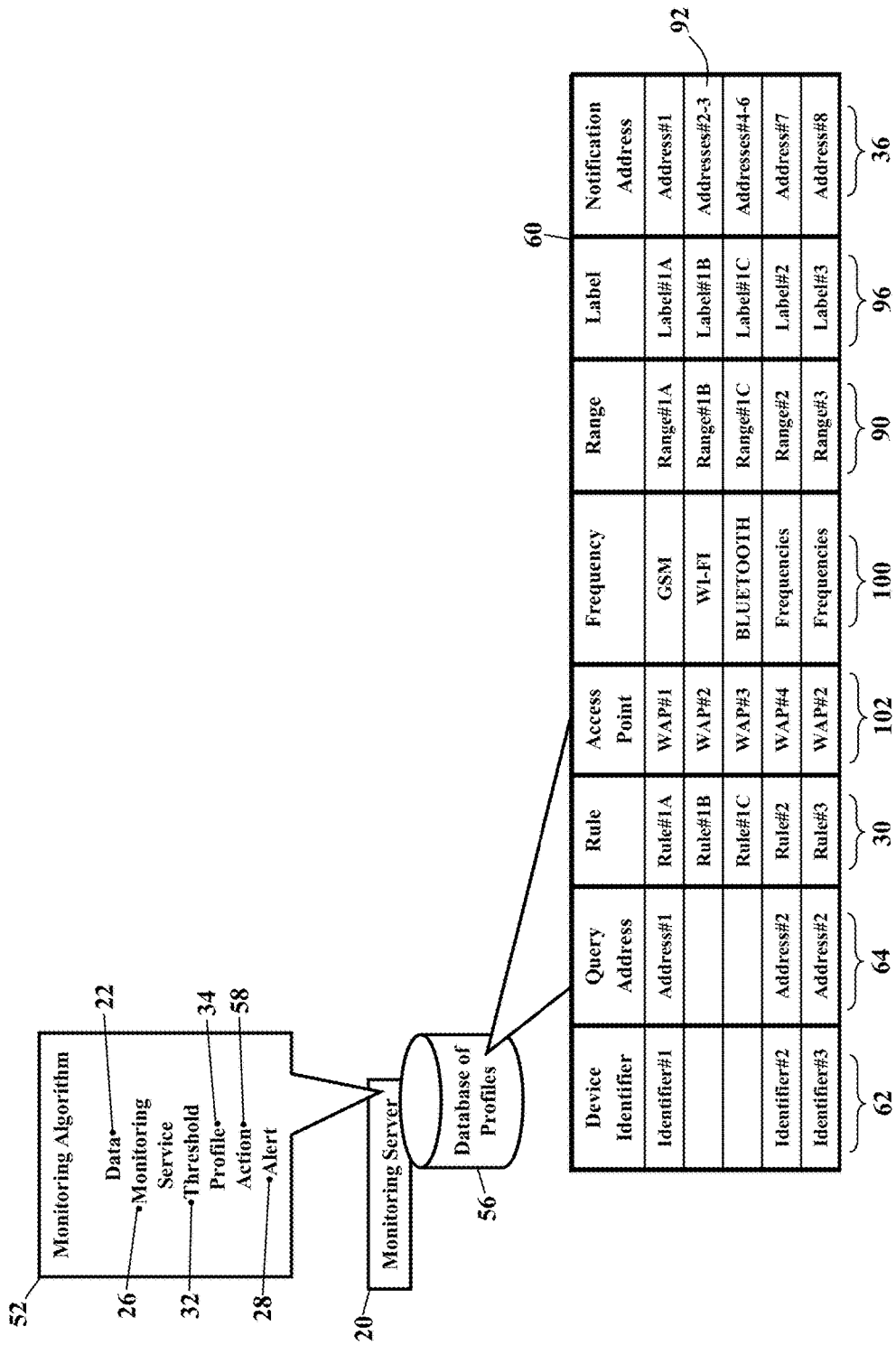

FIGS. 14-15 are more schematics illustrating the profile 34, according to exemplary embodiments. Here the user may configure the profile 34 to distinguish the data 22 according to frequency 100. Some devices that generate the data 22 have multi-channel communications capabilities. That is, some devices may have the capability to send or receive data over different channels or mediums. Some smart phones, for example, may send the data 22 over a cellular network, over a local WI-FI® network, and/or over a BLUETOOTH® network. As the monitoring server 20 collects the data 22, the user's profile 34 may distinguish between the cellular frequencies, the WI-FI® frequencies, and the BLUETOOTH® frequencies. That is, the user may configure her profile 34 to separately analyze the data 22 sent over the cellular network from the data 22 sent over the WI-FI® network and from the BLUETOOTH® network. The rule 30 may thus specify the frequencies 100 associated with the data 22. For example, as FIG. 14 illustrates, a rule 30 may specify that only the data 22 associated with GSM cellular frequencies is analyzed and compared to the corresponding range 90. A different WI-FI® rule 30 may specify that only the data 22 associated with WI-FI® frequencies is retrieved and analyzed. The user may thus also define the corresponding range 90 and the corresponding label 96 and action 58. If either rule 30 is satisfied, the monitoring algorithm 52 instructs the processor 50 to execute the corresponding action 58.

As FIG. 14 illustrates, the label 96 helps distinguish the multi-channel communications capabilities. Because the same device identifier 62 may have different sets of the data 22, and thus the corresponding rules 30 and ranges 90, the monitoring service 26 could produce confusing alerts 28. A single device, in other words, could produce different alerts 28 using the same device identifier 62. Exemplary embodiments help avoid this confusion by establishing different labels 96 for different frequency spectrums. The user may define the label 96 to use different nomenclature terms according to different frequency spectrums. Indeed, some devices may generate the data 22 using any of many different frequency spectrums, such as GSM®, CDMA®, TDMA®, WI-FI®, BLUETOOTH®, and many others. The user may thus configure her profile 34 to separately analyze the data 22 according to the frequency 100, and the label 96 may be defined to identify the analysis by the frequency 100.

FIG. 15 illustrates logical associations to wireless access points, according to exemplary embodiments. Because the data 22 may be distinguished according to the frequency 100, the user may optionally configure the profile 34 with a wireless access point 102 that wirelessly receives the data 22. Data 22 of different frequencies 100 may have different wireless access points 102. A smart phones, for example, may send the data 22 over cellular frequencies 100 to a wireless access point 102 in a cellular network. However, if the smart phone sends the data 22 over a WI-FI® network, a different wireless access point 102 may be used. Indeed, each different frequency 100 may have a different wireless access point 102. As the monitoring server 20 collects the data 22, the user's profile 34 may distinguish between the frequency 100 and/or the wireless access point 102. The profile 34 may thus be configured with different rules 30, ranges 90, labels 96, and notification addresses 36 according to the frequency 100 and/or the wireless access point 102. If the corresponding rule 30 is satisfied, the monitoring algorithm 52 instructs the monitoring server 20 to execute the corresponding action 58.

Exemplary embodiments may thus include a wireless data collector. This wireless data collector may monitor and detect transmissions of any frequency 100. The wireless data collector, for example, may have a receiver that receives transmissions in the WI-FI® and BLUETOOTH® range of frequencies. The receiver may be controlled by a processor that executes an algorithm stored in memory. When the receiver detects a transmission, the processor may intercept a packet of data to read a header and/or payload. The processor may then make a determination as to whether the transmission should be copied or forwarded to the monitoring server 20 for analysis, as the above paragraphs explain.

The wireless data collector may thus be deployed to pickup transmissions of desired frequencies, including USB ports. The wireless data collector may include a microphone to translate sounds, such as high pitched loud alarms from smoke/CO2 detectors or burglar alarms, and to translate spoken phrases into telemetry data for sending to the monitoring server 20.

Figure 16:
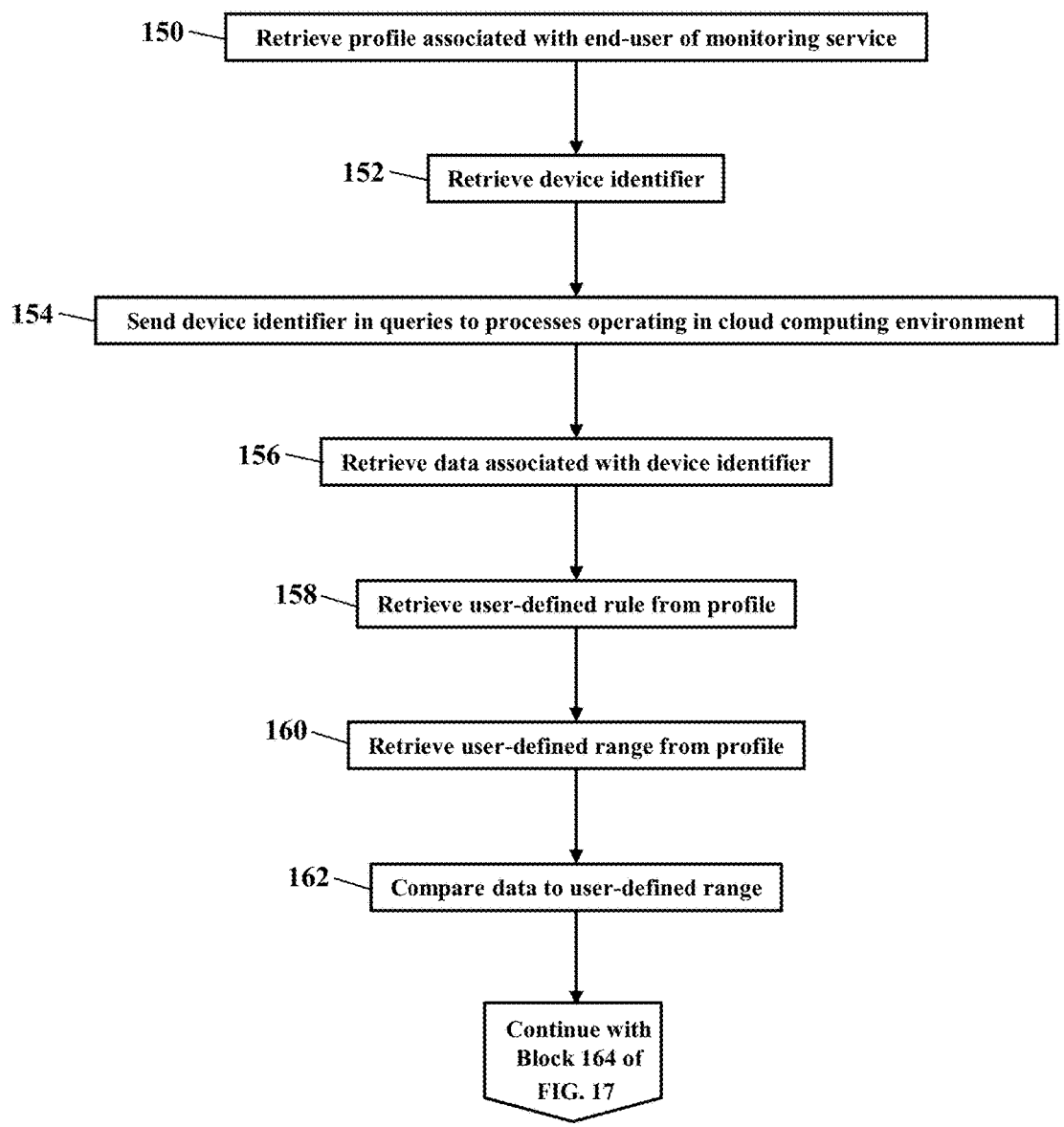
FIGS. 16-17 are flowcharts illustrating a method or algorithm for data monitoring, according to exemplary embodiments.
Figure 17:
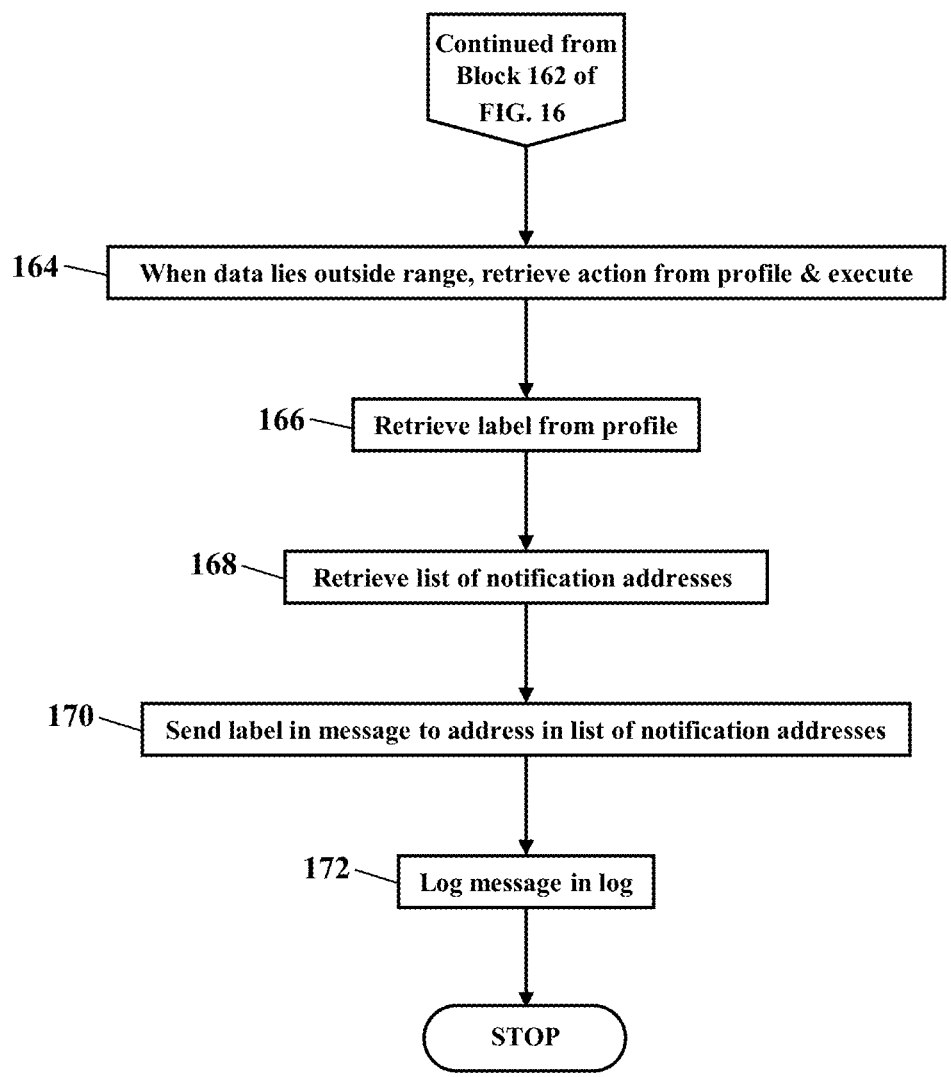

FIGS. 16-17 are flowcharts illustrating a method or algorithm for data monitoring, according to exemplary embodiments. A profile is retrieved that is associated with an end-user of a monitoring service (Block 150). A device identifier is retrieved from the profile (Block 152). The device identifier is sent in queries to processes operating in a cloud computing environment (Block 154). Data associated with the device identifier is retrieved (Block 156). A user-defined rule (Block 158) and range of data (Block 160) is retrieved from the profile. The data is compared to the range of data (Block 162).

The flowchart continues with FIG. 17. When the data lies outside the range, an action is retrieved from the profile and executed (Block 164). A label may be retrieved from the profile (Block 166), along with a list of notification addresses (Block 168). The label is sent in a message to an address in the list of notification addresses (Block 170). The message is logged in a log (Block 172).

Figure 18:
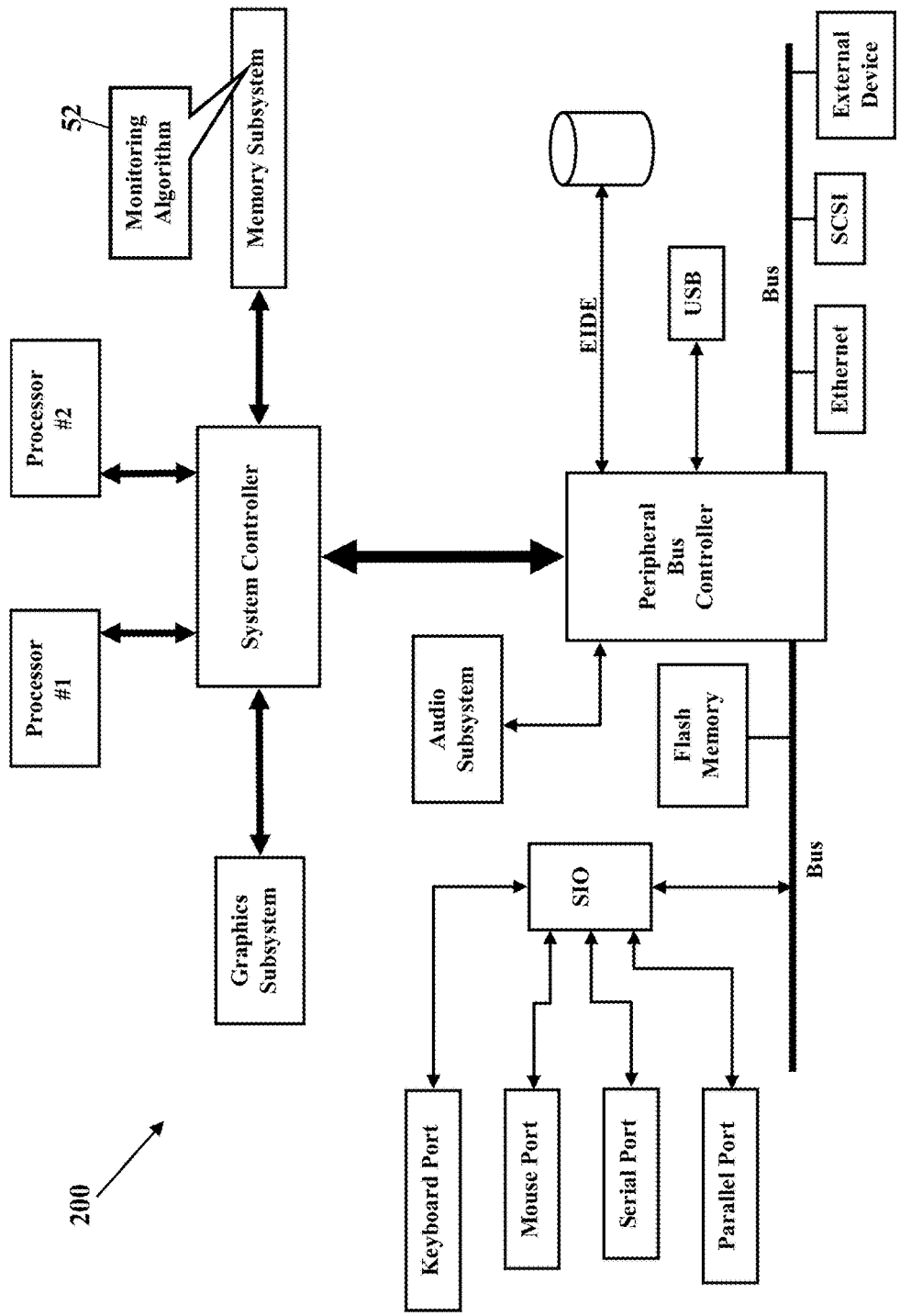
FIGS. 18-19 depict still more operating environments for additional aspects of the exemplary embodiments.

FIG. 18 is a schematic illustrating still more exemplary embodiments. FIG. 18 is a more detailed diagram illustrating a processor-controlled device 200. As earlier paragraphs explained, the monitoring algorithm 52 may operate in any processor-controlled device. FIG. 18, then, illustrates the monitoring algorithm 52 stored in a memory subsystem of the processor-controlled device 200. One or more processors communicate with the memory subsystem and execute either or both applications. Because the processor-controlled device 200 is well-known to those of ordinary skill in the art, no further explanation is needed.

Figure 19:
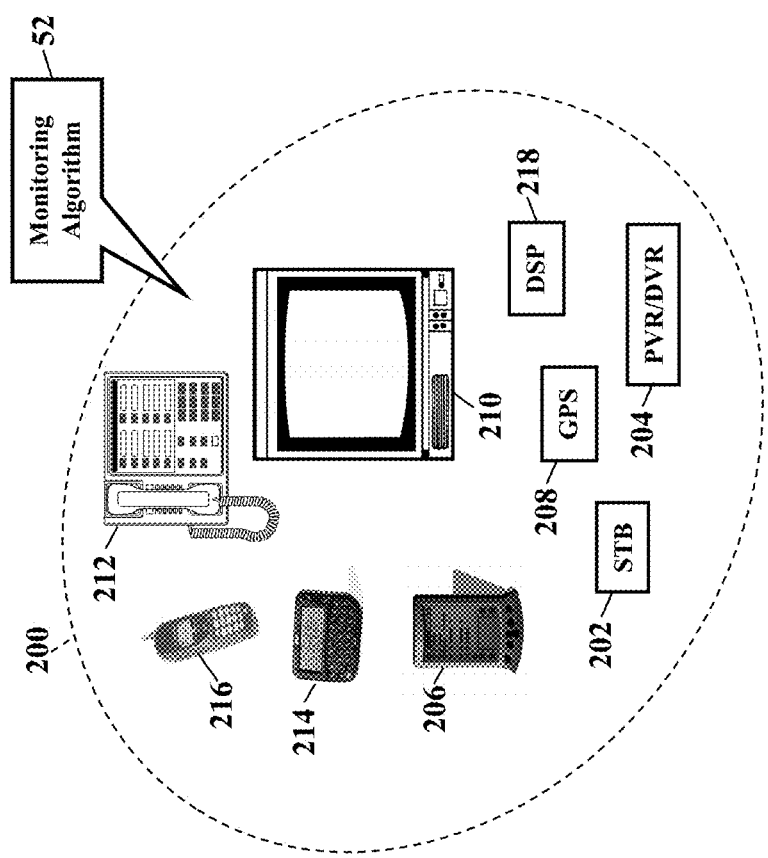

FIG. 19 depicts still more operating environments for additional aspects of the exemplary embodiments. FIG. 19 illustrates that the exemplary embodiments may alternatively or additionally operate within other processor-controlled devices 200. FIG. 19, for example, illustrates that the monitoring algorithm 52 may entirely or partially operate within a set-top box ("STB") (202), a personal/digital video recorder (PVR/DVR) 204, personal digital assistant (PDA) 206, a Global Positioning System (GPS) device 208, an interactive television 210, an Internet Protocol (IP) phone 212, a pager 214, a cellular/satellite phone 216, or any computer system, communications device, or any processor-controlled device utilizing a digital signal processor (DP/DSP) 218. The processor-controlled device 200 may also include watches, radios, vehicle electronics, clocks, printers, gateways, mobile/implantable medical devices, and other apparatuses and systems. Because the architecture and operating principles of the various processor-controlled devices 200 are well known, the hardware and software componentry of the various processor-controlled devices 200 are not further shown and described.

Exemplary embodiments may be physically embodied on or in a computer-readable storage medium. This computer-readable medium, for example, may include CD-ROM, DVD, tape, cassette, floppy disk, optical disk, memory card, memory drive, and large-capacity disks. This computer-readable medium, or media, could be distributed to end-subscribers, licensees, and assignees. A computer program product comprises processor-executable instructions for personalized monitoring of data, as the above paragraphs explained.

While the exemplary embodiments have been described with respect to various features, aspects, and embodiments, those skilled and unskilled in the art will recognize the exemplary embodiments are not so limited. Other variations, modifications, and alternative embodiments may be made without departing from the spirit and scope of the exemplary embodiments.

The invention claimed is:

1. A method, comprising:
   determining, by a server, devices associated with a user;
   sending, by the server, queries to the devices associated with the user, the queries requesting data from the devices;
   receiving, by the server, responses from the devices associated with the user, the responses comprising the data requested by the queries;
   determining, by the server, a combination of the data;
   determining, by the server, an action that is associated with the combination of the data; and
   executing, by the server, the action that is associated with the combination of the data.

2. The method of claim 1, further comprising determining addresses associated with the devices.

3. The method of claim 1, further comprising generating an alert based on at least one of the responses from the devices.

4. The method of claim 1, further comprising generating an alert based on all the responses from the devices.

5. The method of claim 1, further comprising comparing at least one of the responses to a range of values.

6. The method of claim 5, further comprising determining an abnormal condition in response to the at least one of the responses lying outside the range of values.

7. The method of claim 5, further comprising determining a normal condition in response to the at least one of the responses lying within the range of values.

8. A system, comprising:
   a hardware processor; and
   a memory device, the memory device storing instructions, the instructions when executed causing the hardware processor to perform operations, the operations comprising:
   determining devices associated with a user;
   sending queries to the devices associated with the user, the queries requesting data from the devices;
   receiving responses from the devices associated with the user, the responses comprising the data requested by the queries;
   determining a combination of the data requested by the queries;
   determining an action specified by the user; and
   executing the action based on the combination of the data.

9. The system of claim 8, wherein the operations further comprise determining addresses associated with the devices associated with the user.

10. The system of claim 8, wherein the operations further comprise generating an alert based on at least one of the responses from the devices.

11. The system of claim 8, wherein the operations further comprise generating an alert based on the responses from the devices.

12. The system of claim 8, wherein the operations further comprise comparing at least one of the responses from the devices to a range of values.

13. The system of claim 12, wherein the operations further comprise determining an abnormal condition in response to the at least one of the responses lying outside the range of values.

14. The system of claim 12, wherein the operations further comprise determining a normal condition in response to the at least one of the responses lying within the range of values.

15. A memory device storing instructions that when executed cause a hardware processor to perform operations, the operations comprising:
   determining devices associated with a user;
   sending queries to the devices associated with the user, the queries requesting data from the devices;
   receiving responses from the devices associated with the user, the responses comprising the data requested by the queries;
   determining a combination of the data requested by the queries;
   determining an action specified by the user; and
   executing the action based on the combination of the data.

16. The memory device of claim 15, wherein the operations further comprise determining addresses associated with the devices associated with the user.

17. The memory device of claim 15, wherein the operations further comprise generating an alert based on at least one of the responses from the devices.

18. The memory device of claim 15, wherein the operations further comprise generating an alert based on the responses from the devices.

19. The memory device of claim 15, wherein the operations further comprise comparing at least one of the responses from the devices to a range of values.

20. The memory device of claim 15, wherein the operations further comprise determining at least one of an abnormal condition and a normal condition, the abnormal condition in response to the at least one of the responses lying outside the range of values, and the normal condition in response to the at least one of the responses lying within the range of values.

* * * * *